United States Patent [19] [11] 4,329,213
Elwing [45] May 11, 1982

[54] GEL DIFFUSION IMMUNOASSAY INCLUDING α-FETO PROTEIN DETERMINATION

[76] Inventor: Hans B. Elwing, Chalmersgatan 5, 411 35 Gothenburg, Sweden

[21] Appl. No.: 23,193
[22] PCT Filed: Jul. 13, 1978
[86] PCT No.: PCT/SE78/00019
  § 371 Date: Mar. 14, 1979
  § 102(e) Date: Mar. 14, 1979
[87] PCT Pub. No.: WO79/00044
  PCT Pub. Date: Feb. 8, 1979

[30] Foreign Application Priority Data

Jul. 14, 1977 [SE] Sweden ................................ 7708179

[51] Int. Cl.³ .................... G01N 33/54; B01D 57/02; G01N 27/26
[52] U.S. Cl. .............................. 204/180 G; 23/230 B; 424/12
[58] Field of Search ................ 23/230 B; 422/55; 424/12; 204/299 R, 180 G

[56] References Cited

U.S. PATENT DOCUMENTS

| | | | |
|---|---|---|---|
| 3,736,100 | 5/1973 | Rains | 204/180 G X |
| 3,901,870 | 8/1975 | Haupt | 204/180 G X |
| 3,930,983 | 1/1976 | Sieber | 204/180 G X |
| 3,960,488 | 6/1976 | Giaever | 23/230 B |
| 3,960,489 | 6/1976 | Giaever | 23/230 B |
| 3,960,490 | 6/1976 | Giaever | 424/12 X |
| 3,960,491 | 6/1976 | Giaever | 23/230 B |
| 3,960,499 | 6/1976 | White | 422/55 |
| 4,198,389 | 4/1980 | Wadsworth | 204/180 G X |
| 4,200,508 | 4/1980 | Hirai | 204/180 G |

OTHER PUBLICATIONS

H. Elwing et al., Int. Archs. Allergy Appl. Immun., 51, 757–762 (1976).

*Primary Examiner*—Sidney Marantz
*Attorney, Agent, or Firm*—Stevens, Davis, Miller & Mosher

[57] ABSTRACT

A method for the determination of the quantity and type of a first biologically active component in a sample which is added to a well in a liquid-saturated, porous matrix covering a thin layer of a second biologically active component bound to the solid surface of a carrier. A third biologically active component included in the matrix is capable of reacting biospecifically with the first biologically active component when the sample is allowed to diffuse or migrate electrophoretically in the matrix forming a zone containing a precipitate of the first and third biologically active components. This precipitate will absorb with biospecificity to the second biologically active component, bound to the solid surface of the carrier and is visualized in a suitable manner on the surface after removal of the porous matrix, e.g., as a change in the surface tension angle observed with the aid of vapor condensation on the surface. The second and third biologically active components or the second and first biologically active components may be identical as long as the remaining component is capable of reacting with both of the others. All three biologically active components may be antigens and antibodies. The carrier is suitably made of plastic material.

8 Claims, No Drawings

GEL DIFFUSION IMMUNOASSAY INCLUDING α-FETO PROTEIN DETERMINATION

The present invention relates to a biological indicator system based on a two-phase system containing a first biologically active component bound to the surface of a solid phase, and a liquid-saturated immobilized phase covering said surface containing a second biologically active component, capable of reacting with an unknown third biologically active component added to the immobilized phase and permitted to diffuse or migrate electrophoretically during formation of a zone containing a precipitate. The first biologically active component is capable of reacting by absorption with said precipitate formed in the immobilized phase. The presence of the third component is visualized in a suitable manner on the surface, after removal of said immobilized phase.

Serologic testing methods have a central position within the diagnostic techniques of medicine and applied biochemistry in general. This is predominantly due to the fact that such methods afford the possibility of determining minute quantities of the specific reactants in question in complex systems. Within serology there is utilized the basic fact that antibodies (ab) can specifically react with antigens (ag).

When indicating ag-ab-reaction, there are used different secondary manifestations capable of being indicated in various ways. One common method of indicating these reactions is the precipitation technique, in which precipitates are formed under certain conditions when soluble antigens and antibodies come into contact with one another. In certain cases, for example when the antigen is in particle form, agglutination reactions can be utilized, these reactions occurring when antibodies come into contact with the antigen.

In recent years, different types of markers have been used for determining ag-ab-reactions. The markers comprise radioactive isotopes, enzymes, or fluorescent substances which are bound either to the antigen or to the antibody. Indication is then effected by means of the markers in the antigen-antibody-complex, subsequent to separating said complex from non-bound antigen or anti-bodies and accompanying markers.

A specific position is held by the biological determination methods, in which a natural biological effector mechanism is utilized to indicate the antigen-antibody reaction. Among these indication methods can be mentioned complement-binding reactions and different types of neutralizing reactions of biologically active antigenic substances by blocking, for example with virus, toxins, and the like.

Antigen-antibody reactions can be quantified in different ways, by using different indication principles. The most simple of these is the end-point titration method, in which one part of an antigen-antibody system is diluted to a limit at which the indicator system can no longer indicate the reaction.

Another method is one in which indication by means of markers is used, it being necessary to separate the antigen-antibody complex. The amount of labelled reactants in the antigen-antibody complex or in the residue of the system separated therefrom is then determined.

According to one conventional method, one of the reactants, in an antigen-antibody system is incorporated, for example, in an agar gel. The other reactant is supplied in wells disposed in the gel. After some time has lapsed, a radial diffusion gradient is formed by the supplied reactant. The diffusion gradient thus formed is indicated, and the obtained quantification is determined by measuring the area of the circular indication thus formed. It is also known to have the known reactant in the ag-ab-system added to a surface below the gel phase. After diffusion and migration the unknown reactant will react with the known reactant on the surface, where it can be visualized after removing the gel phase.

Indication and quantification of antigen, utilizing known antibodies, are carried out within the field of medical diagnostics and in the follow-up various diseases.

The quantification of an unknown antigen with the aid of known antibodies is effected by immunizing a living organism having the ability to form antibodies against said antigen, whereafter it is possible, with the aid of these antibodies, quantitatively to determine the antigen with which the organism has been immunized. This method has been widely used when quantifying different human serum proteins of the type immunoglobulin and enzymes. In latter years it has also been possible to follow up and diagnose tumorous diseases by determining antigens specific to tumor cells. It has also been found that antibodies can be produced against small molecules having a molecular weight of less than 1000, enabling different types of medicaments and hormones to be shown in serum with the aid of antibodies, for example.

The present invention is suitable for the detection of $\alpha_1$-fe-to-protein, IgG, IsM, IgA, IgE, hepatitis antigen, acute-phase protein, HCG (pregnancy test), and serum proteins in general.

It has now been discovered that an extraordinarily sensitive and readily applied method for determining the quantity and type of biologic substances of the kind in which a component selected from the groups proteins, polysaccharides, nucleic acids, lipids or complexes thereof reacts and where the result of the reaction is visualized in situ with the aid of a component bound to a surface of a solid phase, which is characterized by a system, comprising a first biologically active component bound to the solid surface, and a liquid-saturated immobilized phase located at said surface, said phase containing a second biologically active component, to which is added a test aliquot possibly containing a third biologically active component, which is to be determined, said third component being capable of reacting with the second biologically active component during formation of a precipitate existing of equivalent concentrations of the second and the third component, said precipitate being capable of reacting with the first biologically active component and by the third biologically active component being permitted to diffuse or migrate electrophoretically and form a precipitate with the second biologically active component, said precipitate reacting with the first biologically active component and then removing the immobilized phase, and by reaction between said precipitate and the first component thus being arranged for observing an indication of the presence and quantity of the third component on said solid surface in any suitable manner.

The proteins may comprise immunoglobulins such as antibodies and antigens and other antigenic substances, such as enzymes, toxins, lectins and hormones or systems which form precipitates of the type defined as an equivalent zone precipitate, i.e. where a precipitate is formed when concentration of said second component and said third component are substantially equivalent and therefore forms a moving front of precipitate which is resplit when the concentration of the third biologically active component is increased.

Examples of the polysaccharides include lipopolysaccharides, such as gangliosides, endotoxin, mucopolysaccarides, glycoproteins. Among the lipids, different lipid complexes can be used, such as cardiolipids. Among the nucleic acids, deoxyribonucleic acid has an antigen activity and can be used as a component on the solid surface.

The thin layer of said first component is suitably applied to the solid surface in the following manner: a liquid medium, suitably based on water, is first dispensed onto the solid surface, whereafter a solution containing the component is added to the liquid medium to diffuse therein, whereafter the component is permitted to deposit itself onto the solid surface, becoming bound to the solid surface with a force of such magnitude that said surface can be washed without the layer being removed therefrom, subsequent to the aqueous medium having been removed. The solid surface is suitably a transparent material, such as glass, or a plastics material, e.g. polystyrene, polyacrylonitrile, polyolefines and copolymers thereof.

It has been found in recent years that plastics surfaces advantageously adsorb macro-molecules to form very uniform and reproducible layers. A technique for visualizing antigen-antibody reactions is one in which a thin layer of indium particles is vapor-deposited on a glass surface. The antigen-antibody reactions are carried out on the indium layer, whereafter the reactions can be observed as a light-propagation phenomena on the indium surface. The most serious disadvantages with this technique appear to be the requirement of advanced apparatus for producing a uniform and reproducible layer of indium on large surfaces. This restricts the rational use of such surfaces. Furthermore, it is difficult to classify a reaction as a positive or a negative one, in borderline cases, since this indicator system has a flat amplitude and the indication can only be judged subjectively.

Another, much simpler technique for visualizing adsorbed precipitates on solid surfaces is one employing the condensation of water vapor. This technique involves exposing the dried surface to vapor, whereupon it is possible to determine whether a reaction has taken place and the extent of any such reaction from the pattern formed by the condensation. The principles of this technique were described by Langmuir in 1936. This method is as sensitive as the method employing an indium layer, but has a steeper indication-amplitude. Moreover, it permits the objective analysis by contact-copying of the condensation pattern on the surfaces by irradiation of photographic paper and development thereof.

The indication of ag-ab-reactions is thus best effected with vapor condensation on the plastics surface (Vapour condensation on surface, VCS, see Adams, Klings, Fisher and Vroman, Journal of Immunological Methods, 3, (1973) pages 227–232), which, because of its simplicity, is the preferred method. Other known methods can also be used, such as the so-called ELISA-method (Enzyme-linked immunosorbent assay, J. Immun. 109:129 (1972), mixed haemadsorption (Immunology 9:161 (1965) ), particle adsorption technique, using a slurry of barium sulphate, for example immunofluorescense, various coloring techniques and auto-radiography with isotope-labelled serological reagents.

The reason why it is possible to observe a change as a result of adsorption of precipitates on the molecular layer on the plastics surface as a result of vapor condensation is due to the fact that the so-called Zeta-potential or surface tension against condensed drops of water is changed on the surface when an adsorption reaction has taken place. Such changes are macroscopically visible in the light-scattering phenomena of the condensation pattern. In principle, all hydrophobic surfaces have a surface-tension angle of from 90° to 170°. Those plastics surfaces which normally have such properties include polystyrene, polyacrylonitrile, polyethylene and copolymers thereof.

An immobilized matrix through which the unknown substance shall diffuse is then applied to the surface containing a biologically active component. Such immobilized matrices are well known with the technique of analysis, and may comprise aqueous gels or various types of sediment or fibrous substances. The most conventional method is one in which a gel is used, in particular an agar gel, suitably comprising a buffered 1%-solution of agar which is permitted to solidify. A well is then formed in the matrix, there being supplied to the well a solution containing the unknown component. The unknown component may also be supplied in cellulose plates or the like which have been saturated with the solution containing the unknown component. The system is left at a suitable temperature of between 5° and 50° C., for the unknown substance to diffuse from the well.

Compared with previously known methods of obtaining quantitative measurements of minute quantities of biological materials, the novel method exhibits a simplicity which has not previously been achieved, and therewith a subsequent increase in capacity and decrease of costs. Furthermore on plastics surfaces the precipitation is very uniform and thus suitable for diagnostic tests with regard to reproducibility, which is not the case with glass to the same degree. A further advantage afforded by the use of plastics is that the protein nature of the absorbed component is not denatured or chemically converted, as often happens with glass surfaces. The application of a component fraction by first applying an aqueous medium and then adding the component fraction to said medium ensures that a much more uniform layer is obtained than would be the case when a protein suspension or solution is applied to the dry surface.

Moreover, the amount of component fraction consumed is considerably lower when a plastics surface is used than when a glass substrate is used. Furthermore, when using a glass substrate it is normally necessary to treat the layer with formalin in order to denature the same so that it does not loosen from the glass surface. Finally, the diffusion image obtained on the plastics surface can be treated with antigen-immunoglobulin, thereby to visualize even the most minute reactions or reaction quantities.

This method is based on the experience that immunological precipitation reactions take place when the quantities of antigen and antibody are in a specific relationship to one another and are redissolved when one part or the other is present in large surplus quantities.

In those instances in the aforedescribed method where the matrix contains the said second component in the antigen-antibody reaction, said first component having been added to the plastics surface, and the quantity of the third component is to be determined, it is important that said first component is not added to the surfaces in a pure form, otherwise an excessively large quantity of the second component present in the matrix will bind directly to said first component on said surface as soon as the matrix is applied. In turn, this means that it is impossible, or extremely difficult to read the precipitation-print reaction with any method. It has been found that this problem is removed by mixing said first component with unrelated substances in suitable ratios prior to adding to the plastics surface and thus thin out the layer of said first component.

The method is highly sensitive, and quantities as small as, or less than magnitudes of 10 μg/l can be detected. It is also possible to obtain multi-precipitating systems in which classes of antibodies can be determined. The system enables less pure antigen-antibody substances to be used. It is extremely surprising that precipitation adsorption on the plastics surface is obtained with this technique. This is probably due to the fact that the antibodies have two binding functions, and that there is obtained a bond with said first component located on the solid surface and a further agglomerating and cross-linking bond with the antigens in the matrix. Thus, the matrix contains one or more antibodies against the antigen to be determined, and the solid surface is provided with this antigen or another antigen, whereby complex reactions can be obtained.

It is also possible to obtain multiple precipitation zones if said third component includes more than one biologically active element and if the immobilized phase containing said second component consisting of more than one element, which reacts with the respective element in the third component. The multiple zones thus obtained can be selectively combined with said first component if the latter consists of separate areas each covered with a different compound reacting with the respective precipitate to provide individual detection.

From the above description it will be evident that the said first and said third component can be the same if the second is different and the said first and said second component can also be the same if the said third component is different, of course, all three could be of different kinds. Thus, if said second component is an antibody said third component can be an antigen and said first component can be either an antibody like or unlike said second component or an antigen like or unlike said third component.

As an example, said first component is the antigens IgG and IgA, each on its own surface area. Said second component consists of anti-IgG, anti-IgG and anti-IgM and said third component consists of a human serum containing IgA, IgG and IgM. The serum is placed in a well on the borderline between the two different surface areas of said first compound. After a suitable diffusion period three concentric precipitation lines can be observed and measured in the gel. The gel is then removed and it is possible to record the respective positions of the IgA and IgG precipitates. The third precipitate is identified by exclusion as the IgM precipitate.

In another embodiment according to the invention, said first component in anti-α-feto-protein. Anti-α-feto-protein is included in the gel in such a low concentration that no visible precipitate can be obtained with said third component, which is α-feto-protein in human serum. α-feto-protein is an indication of primary hepathomas, which are types of tumors. α-feto-protein is present in very low concentration in early cases of tumors, and can thus be observed by a precipitation reaction at the surface area, where said first and said second components together form the precipitate.

The use of low concentrations of anti-α-feto-protein in the gel make this method more sensitive. There will only be precipitation if the original concentration of said third component in the sample is higher than the concentration of said second component.

I claim:

1. A method of determining the quantity and type of biologic substances of the kind in which a component selected from the group consisting of proteins, polysaccharides, nucleic acids, lipids, and complexes thereof biospecifically reacts and where the result of the reaction is visualized in situ with the aid of a component bound to the surface of a solid, comprising
    a. providing a system containing (1) a first biologically active component bound to a solid surface and (2) a liquid-saturated immobilized phase located at said solid surface and containing a second biologically active component,
    b. adding to said system a test aliquot containing a third biologically active component to be determined, said third biologically active component capable of reacting with said second biologically active component in said immobilized phase to form a precipitate containing equivalent concentrations of said second biologically active component and said third biologically active component,
    c. permitting said third biologically active component to diffuse or migrate electrophoretically and form a precipitate with said second biologically active component in said immobilized phase,
    d. reacting said precipitate with said first biologically active component,
    e. removing said immobilized phase, and
    f. detecting the presence or quantity of said third biologically active component on said solid surface.

2. The method of claim 1 wherein said first biologically active component and said second biologically active component are identical.

3. The method of claim 1 wherein said first biologically active component and said third biologically active component are identical.

4. The method of claim 1 wherein said solid surface is provided by a plastic selected from the group consisting of polystyrene, polyacrylonitrile, polyolefins, and copolymers thereof.

5. The method of claim 1 wherein the detection of step f. is carried out by observing any change in the surface tension angle of vapor condensed on said surface.

6. The method of claim 1 wherein said first and second biologically active components are anti-α-feto-protein and said third biologically active component is α-feto-protein contained in human serum.

7. The method of claim 1 wherein (a) said solid surface has different sectors covered with different components active as said first biologically active component, (b) more than one component is incorporated in said immobilized phase acting as said second biologically active component, and (c) different reactions are indicated at different surface sectors after removing said immobilized phase.

8. The method of claim 7 wherein 7 (a) IgA and IgG are used as said first biologically active component on different sectors of said surface, (b) said immobilized phase contains anti-IgA, anti-IgG, and anti-IgM, and (c) said third biologically active component is human serum containing at least one of IgA, IgG, and IgM.

* * * * *